United States Patent [19]

Schindler et al.

[11] 4,353,824
[45] Oct. 12, 1982

[54] CHROMOPHORIC CEPHALOSPORINS

[75] Inventors: Peter Schindler, Rodgau; Gerhard Huber, Kelkheim, both of Fed. Rep. of Germany

[73] Assignee: Hoechst Aktiengesellschaft, Frankfurt am Main, Fed. Rep. of Germany

[21] Appl. No.: 142,767

[22] Filed: Apr. 22, 1980

[30] Foreign Application Priority Data

Apr. 24, 1979 [DE] Fed. Rep. of Germany ....... 2916433

[51] Int. Cl.³ ............................................ C07D 501/38
[52] U.S. Cl. ................................... 260/156; 260/153; 260/154; 424/246; 544/25; 544/22; 435/18; 435/34; 435/38
[58] Field of Search ............... 544/25, 21, 26, 30, 544/22, 16, 25; 260/156, 155, 153, 154; 424/270, 246

[56] References Cited

U.S. PATENT DOCUMENTS 4,024,134  5/1977  Gregson et al. .................... 544/28

*Primary Examiner*—Nicholas S. Rizzo
*Attorney, Agent, or Firm*—Curtis, Morris & Safford

[57] ABSTRACT

What are disclosed are cephalosporins of the formula

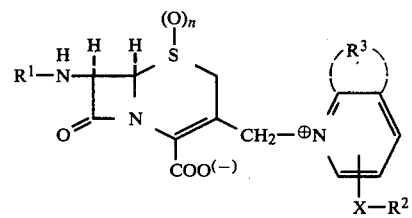

processes for the manufacture of said cephalosporins, preparations containing same for the detection of β-lactamases, a process for making said preparations, and the use of said cephalosporins for the detection of β-lactamases.

3 Claims, No Drawings

CHROMOPHORIC CEPHALOSPORINS

The therapeutical utility of β-lactam antibiotics is restricted by the occurrence of β-lactam resistant bacteria. The resistance is causally connected with the formation of β-lactamases (penicillin-(cephalosporin)-β-lactam-aminohydrolases, EC 3.5.2.6) which hydrolyze the C-N bond of the β-lactam ring of penicillins and cephalosporins, whereby the antibiotic properties of said compounds are lost. To ensure the desired success of the therapy when treating bacterial infections with β-lactam antibiotics, knowledge is required, prior to starting the therapy, whether the clinical isolates produce β-lactamases or not. If the β-lactamase test is positive, it is recommended to use β-lactamase resistant antibiotics or other antibiotics suitable for clinical use.

To detect germs producing β-lactamase, a series of techniques has been described (cf. J. Pharmacol. 15, pages 81 to 91 (1963)). However, the methods are not all fully satisfactory because, as far as colorimetric tests-which are especially suitable for clinical-diagnostic purposes-are concerned, they all require the addition of an indicator (iodine/starch, hydroxylamine, pH-indicator).

As compared with the β-lactamase tests with the aid of such coupled test procedures, chromogenic β-lactamase substrates have the advantage that the opening of the β-lactam ring by these enzymes directly results in a color change in the visible part of the spectrum. A substrate of this type (compound 87/312) has been described by O'Callaghan et al. (Antimicrob. Ag. Chemother. 1, pages 283–288 (1972)). According to the statements of the authors, a bathochromic change of the color of solutions of compound 87/312 takes place not only in the presence of β-lactamases, but also in a non-specific manner after addition of serum, animal tissue, protein, milk, cysteine, glutathione, mercaptoethanol and 2,3-dimercaptopropanol-1. This may lead to a false judgement of clinical isolates.

It is, therefore, the object of the present invention to provide novel, chromophoric cephalosporins as β-lactamase substrates which are characterized by a distinctly visible color change, for example from an intense violet to yellow, which are well suitable for the detection of germs producing β-lactamase and for the determination of the activity of isolated, β-lactamase-producing germs and of isolated β-lactamases, and which are stable to the aforesaid additives.

The compounds of the invention are split by all tested β-lactamases from gram-negative organisms, especially by the enzymes of clinically interesting organisms such as E. coli R$_{TEM}$, Klebsiella aerogenes 1082 E, Pseudomonas aeruginosa 18 SH, Enterobacter cloacae P 99 and Bacteroides fragilis 620. The compounds of the invention are also split by β-lactamases of gram-positive organisms, for example Staphylococcus aureus R 85. The compounds can also be used for the detection of germs producing β-lactamase, i.e. β-lactamases with intact cells of these organisms.

The β-lactamase activity is directly tested with the compounds of the invention, i.e. without coupled test procedures, because the chromophoric substituents of the invention are quantitatively eliminated synchronously with the opening of the β-lactam ring, which directly leads to the color change (specific for the individual substituents).

It has surprisingly been found that, in contradistinction to β-lactamase substrates of the type 87/312, the compounds of the invention are extremely stable to hydrolytic degradation in a temperature range of from −180° C. to 60° C. in aqueous solutions suitable for the activity of the β-lactamases and the viability of bacteria. Although solutions ready for use are preferably stored at −20° C., at which temperature their stability is practically unlimited, neutrally buffered solutions can be kept at refrigerator temperature for a prolonged period of time and even at room temperature without their usability being impaired.

In addition, the compounds of the invention are completely stable to the influence of serum, protein, milk, cysteine, glutathione, mercaptoethanol and 2,3-dimercaptopropanol-1 (dimercaprol), which constitutes a further surprising advantage over β-lactamase substrates of the type 87/312.

It is, therefore, the object of the present invention to provide cephalosporins carrying a chromophoric grouping in the 3-position and having the formula I

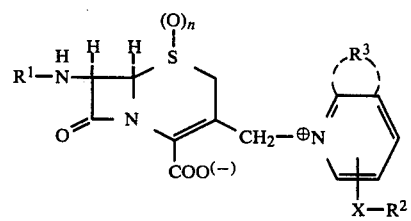

in which
R$^1$ is hydrogen, formyl or a radical of the formula

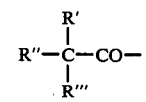

in which R' is hydrogen, optionally substituted alkyl having 1 to 4 carbon atoms, an optionally substituted, saturated or mono- or poly- unsaturated carbocyclic ring, optionally substituted aryl or aryloxy, optionally substituted heteroaryl or heteroarylthio, R" and R''', which are identical or different, taken alone are hydrogen, alkyl with 1 to 4 carbon atoms, hydroxy, optionally substituted acyloxy with 1 to 4 carbon atoms in the acyl moiety, optionally substituted alkoxy with 1 to 4 carbon atoms in the alkyl moiety, amino, optionally substituted alkylamino, optionally substituted acylamino, alkoxycarbonyl with 1 to 4 carbon atoms in the alkyl moiety, halogen, cyano, sulfoxy, or aminosulfonyl, or taken together denote oxygen, X is

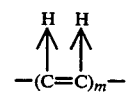

with m being 1 to 4, or —N=N— or combinations of said groups,
R$^2$ is optionally substituted phenyl,
R$^3$ stands for 2 hydrogen atoms or an annellated aromatic or hetero-aromatic ring and
n is zero or 1 or 2.

The radical —X—R$^2$ can be in alpha-, beta- or gamma-position of the pyridinium ring.

Preferred compounds of the invention are those of the formula II

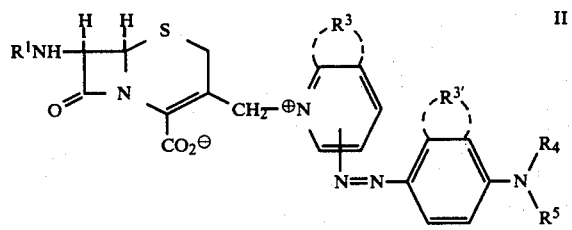

in which

R$^1$ and R$^2$ are as defined under formula I,

R$^{3'}$ has one of the meanings given for R$^3$ and

R$^4$ and R$^5$, which are identical or different, are hydrogen or alkyl with 1 to 4 carbon atoms which may be substituted by halogen, hydroxy, acyloxy with 1 to 4 carbon atoms, alkoxy with 1 to 4 carbon atoms, alkoxycarbonyl with 1 to 4 carbon atoms in the alkoxy moiety, carboxy, cyano, aminocarbonyl or sulfoxy.

The linkage of the aminophenyl-diazo group with the pyridinium nucleus gives different compounds IIa, IIb and IIc of the invention depending on the respective position.

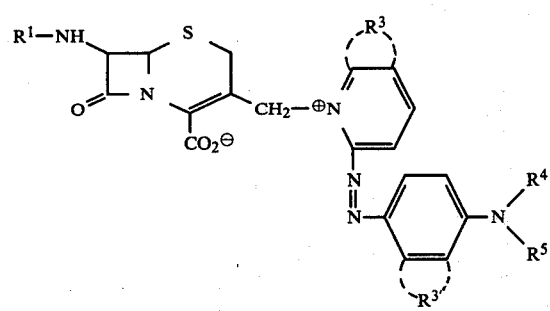

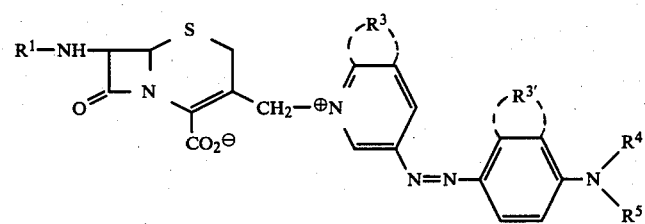

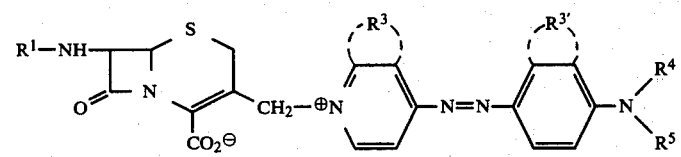

More particularly, in the compounds of the invention the substituents are as follows:

R' denotes hydrogen, alkyl with 1 to 4 carbon atoms, preferably methyl or ethyl, substituted alkyl with 1 to 4 carbon atoms, for example haloalkyl with 1 to 4 carbon atoms, preferably chloromethyl, bromomethyl, chloroethyl or bromoethyl, cyanoalkyl with 1 to 4 carbon atoms in the alkyl moiety, preferably cyanomethyl or cyanoethyl, hydroxyalkyl with 1 to 4 carbon atoms, preferably hydroxymethyl or hydroxyethyl, alkoxyalkyl with 1 to 4 carbon atoms in the alkoxy as well as in the alkyl moiety, preferably methoxymethyl, ethoxymethyl or methoxyethyl, ω-carboxy-ω-aminoalkyl with 1 to 4 carbon atoms in the alkyl moiety, preferably ω-carboxy-ω-aminopropyl, ω-carboxy-ω-acylaminoalkyl with 1 to 4 carbon atoms in the alkyl moiety and 1 to 7 carbon atoms in the acyl moiety, preferably ω-carboxy-ω-benzoylaminopropyl, ω-carboxyalkyl with 1 to 4 carbon atoms in the alkyl moiety, preferably carboxymethyl or carboxyethyl, a possibly substituted, saturated or mono- or polyunsaturated, 5- to 7-membered carbocyclic ring, for example cycloalkyl, preferably cyclohexyl, cycloalkenyl, preferably cyclohexyl, cycloalkadienyl, preferably cyclohexadienyl, possibly substituted aryl or aryloxy of the formulae

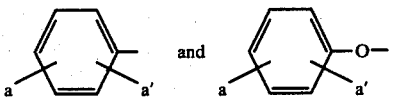

in which a and a' are identical or different and denote hydrogen, C$_1$-C$_4$ alkyl, preferably methyl or ethyl, hydroxy, C$_1$-C$_4$alkoxy, preferably methoxy or ethoxy, C$_1$-C$_4$acyloxy, preferably acetoxy, halogen, preferably fluorine and chlorine, carboxy, sulfoxy, amino, C$_1$-C$_4$acylamino, preferably acetylamino. R' may also denote optionally substituted, 5 or 6-membered heteroaryl containing nitrogen, sulfur or oxygen as heteroatoms, for example 2-pyridon-1-yl, 4-pyridon-1-yl, 3,5-dichloropyridon-1-yl, 2-thienyl, 3-thienyl, 2- and 3-furyl, tetrazolyl, preferably 2-furyl, 2-thienyl, 1-tetrazolyl or thiazolyl of the formula

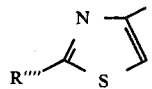

in which

R'''' preferably denotes alkyl with 1 to 4 carbon atoms, especially methyl or ethyl, amino, optionally substituted acylamino, especially formamido, acetamido, chloroacetamido, bromoacetamido, or trifluoroacetamido. R' may also denote an optionally substituted heteroaryl radical, preferably 2-methyl-1,3,4-thiadiazol-5-yl-thio or 2-amino-1,3,4-thiadiazol-5-yl-thio.

R'' and R''', which are identical or different, may be hydrogen, alkyl with 1 to 4 carbon atoms, preferably methyl, hydroxy, optionally substituted acyloxy with 1 to 4 carbon atoms in the acyl moiety, for example formyloxy, acetoxy, propionyloxy, optionally substituted alkoxy with 1 to 4 carbon atoms in the alkyl moiety, for example methoxy, ethoxy, propoxy, amino, optionally substituted alkyl amino, preferably tert.butylamino, tert.amylamino, benzylamino, p-methoxybenzylamino, benzhydrylamino, tritylamino, phenylethylamino, optionally substituted acyl amino, for example formylamino, acetylamino, chloroacetylamino, bromoacetylamino, benzoylamino, tert.butoxycarbonylamino, 2,2,2-trichloroethoxycarbonylamino, 4-hydroxy-1,5-naphthyridin-2-carbonylamino, 3-hydroxy-pyridazin-4-carbonylamino, imidazolidin-2-on-1-yl-carbonylamino, (3-methyl-sulfonyl-imidazolidin-2-on-1-yl)-carbonylamino, (4-ethyl-piperazin-2,3-dion-1-yl)-carbonylamino, alkoxycarbonyl with 1 to 4 carbon atoms in the alkyl moiety, for example methoxycarbonyl, ethoxycarbonyl, halogen, preferably chlorine and bromine, cyano, sulfoxy, aminosulfonyl or taken together R'' and R''' denote oxygen, X is preferably —N=N—, $R^2$ is phenyl which may be substituted by hydroxy, alkoxy with 1 to 4 carbon atoms, preferably methoxy and ethoxy, acyloxy with 1 to 4 carbon atoms, preferably acetoxy and propionyloxy, but preferably by a group of the formula

in which $R^4$ and $R^5$ are identical or different and denote hydrogen, alkyl with 1 to 4 carbon atoms, preferably methyl and ethyl, cyanoalkyl with 1 to 4 carbon atoms in the alkyl moiety, preferably cyanoethyl, carboxyalkyl with 1 to 4 carbon atoms in the alkyl moiety, preferably carboxyethyl, alkoxycarbonylalkyl with 1 to 4 carbon atoms in each alkyl moiety, preferably ethoxycarbonyl-ethyl, hydroxyalkyl with 1 to 4 carbon atoms, preferably hydroxyethyl, or acyloxyalkyl with 1 to 4 carbon atoms in the acyl and alkyl moiety, preferably acetoxyethyl, aminocarbonylalkyl with 1 to 4 carbon atoms in the alkyl moiety, preferably aminocarbonylethyl, sulfoxyalkyl with 1 to 4 carbon atoms, preferably sulfoxyethyl, haloalkyl with 1 to 4 carbon atoms, preferably chloroethyl.

$R^3$ and $R^{3'}$ can be identical or different and denote two hydrogen atoms, a connected aromatic ring, preferably benzo or a connected heteroaromatic 5- or 6-membered ring with 1 or 2 heteroatoms, especially nitrogen and/or sulfur, preferably pyrido, thieno, pyrimidino, thiazolo.

It is another object of the present invention to provide a process for the manufacture of cephalosporins of the formula I, which comprises reacting a compound of the formula III

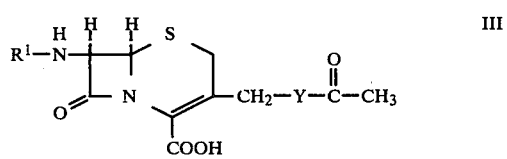

in which $R^1$ is as defined for formula I and Y denotes oxygen or sulfur with a compound of the formula IV

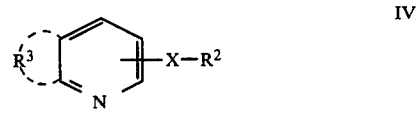

in which $R^2$, $R^3$ and X are as defined for formula I.

For the manufacture of the preferred compounds of the formula II, compounds of the formula III are reacted with compounds of the formula IVa

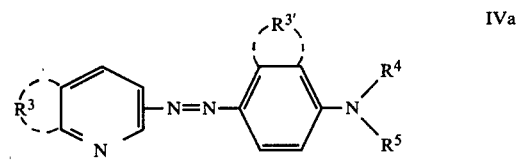

in which $R^3$, $R^{3'}$, $R^4$ and $R^5$ are as defined above.

Thus, the especially preferred 7-thienyl-2-acetamido)-3-[2-(4,N,N-dimethylaminophenylazo)-pyridinium-methyl]-3-cephem-4-carboxylic acid of the formula

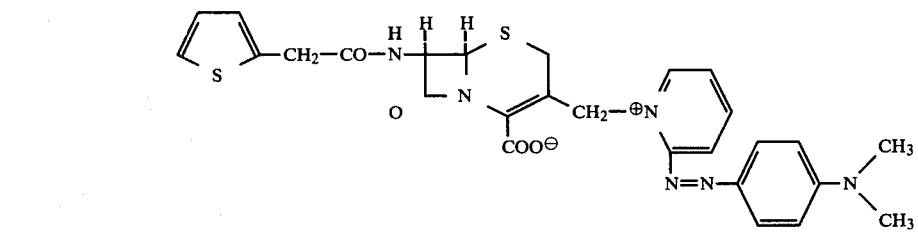

also named PADAC (pyridine-azo-dimethylanilino-cephalotin), can be prepared by reacting the compound PADA (trans-pyridine-azo-p-dimethylaniline) of the formula

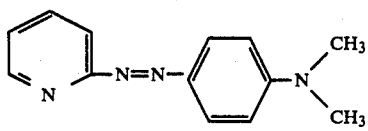

with cephalotin of the formula

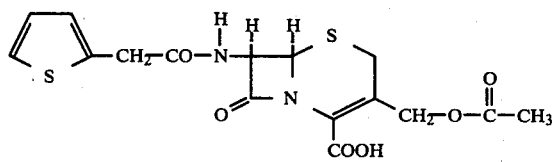

The starting compounds used to carry out the process of the invention are known from the literature or can be prepared by processes described in literature.

The reaction of compound III with compound IV, preferably with compound IVa, is suitably carried out in an aqueous medium, with addition of solvents miscible with water, such as methanol, ethanol, isopropanol, acetonitrile or acetone, to improve the solubility. The reaction components can be used in any desired ratio, preferably, however, in molar proportion. The reaction is carried out at a temperature from about 20° to 80° C., preferably 55° to 65° C. During the reaction the pH of the reaction solution is maintained at about 5 to 8, preferably 6.5 to 7.5, while adding with stirring, for example, sodium hydroxide solution or saturated sodium bicarbonate solution.

To facilitate the reaction, potassium iodide or potassium thiocyanide (for example about 5 to 20, preferably 10 to 15 mols per mol of cephalosporin used) can be added to the reaction medium.

When the reaction is terminated, the reaction products of the invention are isolated. To this end, the solvent miscible with water, for example acetone, is distilled off and to remove unreacted portions of compound IV or IVa, for example PADA, the aqueous phase is extracted with ethyl acetate or another suitable solvent. The reaction compounds can be obtained from the aqueous phase by precipitation at a pH of about 2 to 4, preferably 3, or by extraction with methylene chloride or another suitable organic solvent at the same pH. After concentration of the extract in vacuo, the reaction products can be precipitated by adding an organic solvent in which they are sparingly soluble, for example diethyl ether or petroleum ether.

According to another variant of the process of the invention, the compounds of the formula I can be prepared by reacting compounds of the formula III in which $R^1$ is hydrogen with a compound of the formula IV in the manner described above and the chromophoric compound of the formula I obtained in which $R^1$ is hydrogen is reacted in known manner with a carboxylic acid of the formula V

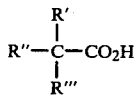 V in which R′, R″ and R‴ are as defined above, or with an activated derivative of said carboxylic acid.

Suitable activated derivatives of carboxylic acids of the formula V are, in the first place, the halides, preferably chlorides and bromides, anhydrides and mixed anhydrides, azides and activated esters preferably those with p-nitrophenol, 2,4-dinitrophenol, methylene cyanohydrin, N-hydroxysuccinimide and N-hydroxyphthalimide, more preferably 1-hydroxybenzotriazole and 6-chloro-1-H-hydroxybenzotriazole. Suitable mixed anhydrides are preferably those with lower alkanoic acids, for example acetic acid and more preferably with substituted acetic acids, for example trichloroacetic acid, pivalic acid, or cyanoacetic acid. Especially preferred are also mixed anhydrides with carbonic acid semiesters, as obtained, for example, by reacting the carboxylic acids of the formula V with chloroformic acid benzyl ester, chloroformic acid p-nitrobenzyl ester, chloroformic acid isobutyl ester, chloroformic acid ethyl ester, or chloroformic acid allyl ester. The activated derivatives can be reacted in the form of isolated substances or in situ. In general, the cephem derivative of the formula I in which $R^1$ is hydrogen is reacted with the carboxylic acid of the formula V or an activated derivative thereof in the presence of an inert solvent. Especially suitable inert solvents are chlorinated hydrocarbons, preferably methylene chloride and chloroform; ethers, for example diethyl ether, diisopropyl ether and more preferably tetrahydrofurane and dioxane; ketones, preferably acetone and butanone; amides, preferably dimethyl formamide and dimethyl acetamide; or water. It may prove advantageous to use mixtures of the said solvents. This is often the case for the reaction of a cephem compound of the formula I in which $R^1$ is hydrogen with an activated derivative of the carboxylic acid of the formula V produced in situ.

The reaction of cephem compounds of the formula I in which $R^1$ denotes hydrogen with carboxylic acids of the formula V or the activated derivatives thereof can be carried out at a temperature in the range of from about $-50°$ to about $+80°$ C., preferably $-20°$ to $+50°$ C. and more preferably $-20°$ C. to room temperature.

The time of reaction depends on the reactants used, the temperature and the solvent or solvent mixture used and normally is in the range of from about 15 minutes to about 72 hours.

The reaction of activated derivatives of the carboxylic acids of the formula V with cephem compounds of the formula I in which $R^1$ is hydrogen is preferably carried out in an alkaline medium at a pH above 7. To this end a base is added to the reaction mixture, preferably potassium or sodium carbonate, potassium or sodium bicarbonate, potassium or sodium hydroxide, pyridine, or a trialkyl amine, for example triethyl amine, N-methylmorpholine, ethyl diisopropyl amine, or potassium tert.butylate.

The cephalosporins obtained according to the invention can be purified in known manner by chromatography on silica gel, cellulose, Sephadex G-10, G-25, or LH-20, adsorption resins such as Amberlite XAD-2 and XAD-4 or Diaion HP-20.

The especially preferred PADAC mentioned above has an intense violet color ($\lambda_{max}$ 566 nm) which turns to yellow ($\lambda_{max}$ 465 nm) after reaction with β-lactamases, for example a β-lactamase of *Enterobacter cloacae* P 99. An analogous reaction takes place with other β-lactamases, for example from *Escherichia coli* $R_{TEM}$, *Klebsi-* ella aerogenes 1082 E, *Enterobacter cloacae* P 99, Pseudomonas aeruginose 18 SH, *Bacteroides fragilis* 620 and *Staph. aureus* R 85. Other chromophoric cephalosporins according to the invention exhibit a corresponding change in color in the reaction with β-lactamases.

For the detection of β-lactamases, solutions of the chromophoric cephalosporins buffered so as to be neutral are admixed directly with isolated β-lactamases or with cell suspensions of germs producing β-lactamases. With an appropriate selection of the cephalosporin concentration, a change in color characteristic for the individual compounds is observed. The β-lactamase proof can also be carried out by diluting the compounds of the invention not in a buffer solution but in hot agar-agar solution containing all nutrients necessary for the growth of bacteria. The clinical samples to be tested are then applied in appropriate dilution onto the test dishes made in usual manner. After incubation of the test dishes at temperatures depending on the specific requirements of the germs to be examined, the same change in color can be observed in the neighbourhood of the bacteria producing β-lactamase. Alternatively, clinical samples obtained in different manner can be spread in the form of a colony smear on a wetted test strip of paper or another suitable carrier material, for example absorbent plastic material, dextrans or other natural polymers, which has previously been impregnated with appropriate, preferably aqueous, solutions of the compounds of the invention. In this case, too, the characteristic change in color can be observed within a short period of time.

Besides the compounds specified in the examples, the following compounds II can be prepared by the process of the invention.

| formula | $R^1$ | $R^3$ | $R^{3'}$ | $R^4$ | $R^5$ |
|---|---|---|---|---|---|
| IIa | CH$_3$CO | H,H | H,H | CH$_3$ | CH$_3$ |
| IIa | C$_3$H$_7$CO | " | " | " | " |
| IIa | CH$_3$OCH$_2$CO | " | " | " | " |
| IIa | " | " | " | C$_2$H$_5$ | C$_2$H$_4$CO$_2$H |
| IIa | NCCH$_2$CO | " | " | —CH$_2$CH$_2$OCOOH$_3$ | CH$_2$CH$_2$OCOCH$_3$ |
| IIa | NCCH$_2$—S—CH$_2$CO | " | " | CH$_3$ | CH$_3$ |
| IIa | " | " | " | " | CH$_2$CH$_2$CN |
| IIa | " | " | " | " | CH$_3$ |
| IIa |  HO—⟨phenyl⟩—CH$_2$CO— | " | " | C$_2$H$_5$ | CH$_2$CH$_2$CO$_2$H |
| IIb |  ⟨phenyl⟩—CH$_2$CO— | " | " | " | " |
| IIb | " | " | " | " | C$_2$H$_5$ |
| IIa | " | " | " | CH$_3$ | CH$_2$CH$_2$CN |
| IIb | " | " | " | H | CH$_2$CH$_2$CO$_2$H |
| | | | | ⟨pyridyl N⟩ | |
| IIc |  ⟨thienyl⟩—CH$_2$—CO— | " | H,H | CH$_3$ | CH$_3$ |
| IIc | " | " | " | C$_2$H$_5$ | C$_2$H$_5$ |
| IIc | " | " | " | —CH$_2$CH$_2$OCOCH$_3$ | CH$_2$CH$_2$OCOCH$_3$ |
| IIa |  ⟨phenyl⟩—OCH$_2$CO— | " | " | C$_2$H$_5$ | C$_2$H$_5$ |
| IIa | " | " | " | CH$_3$ | CH$_2$CH$_2$CN |
| IIa | " | " | " | CH$_2$CH$_2$CN | CH$_2$CH$_2$OCOCH$_3$ |
| IIb |  ⟨phenyl⟩—OCH$_2$CO | " | H | C$_2$H$_5$ | C$_2$H$_5$ |
| IIb | " | " | " | C$_2$H$_5$ | CH$_2$CH$_2$CO$_2$H |
| IIb | " | " | " | H | C$_2$H$_4$CO$_2$H |
| | | | | ⟨pyridyl N⟩ | |
| IIc | " | " | H,H | CH$_3$ | CH$_3$ |
| IIc | " | " | " | C$_2$H$_5$ | C$_2$H$_5$ |
| IIa |  H$_2$N—⟨aminothiazolyl⟩—CH$_2$—CO— | " | " | CH$_3$ | CH$_3$ |
| IIa | " | " | " | C$_2$H$_5$ | C$_2$H$_5$ |
| IIa | " | " | " | C$_2$H$_4$OCOCH$_3$ | C$_2$H$_4$OCOCH$_3$ |
| IIb | " | " | " | CH$_3$ | CH$_3$ |
| IIb | " | " | " | C$_2$H$_5$ | C$_2$H$_4$CO$_2$H |
| IIc | " | " | " | CH$_3$ | CH$_3$ |

-continued

| formula | $R^1$ | $R^3$ | $R^{3'}$ | $R^4$ | $R^5$ |
|---|---|---|---|---|---|
| IIa | $CH_3\text{-}C(=N)\text{-}S\text{-}CH_2-$ | " | " | $CH_3$ | $CH_3$ |
| IIa | " | " | " | $CH_2CH_2OCOCH_3$ | $CH_2CH_2CN$ |
| IIa | " | " | " | $CH_3$ | " |
| IIb | " | " | " | $C_2H_5$ | $C_2H_5$ |
| IIb | " | " | " | $C_2H_5$ | $C_2H_4CO_2H$ |
| IIb | " | " | " | $C_2H_5$ | $C_2H_4CN$ |
| IIa | thienyl-$CH_2CO$ | H,H | H,H | $C_2H_5$ | $C_2H_4\text{—}OSO_3H$ |
| IIb | " | " | " | " | " |
| IIa | phenyl-$CH_2CO$ | " | " | " | " |
| IIb | " | " | " | " | " |
| IIa | phenyl-$OCH_2CO$ | " | " | " | " |
| IIb | " | " | " | " | " |
| IIa | $CO_2H\text{-}CH(NH_2)\text{-}(CH_2)_3\text{-}CO$ | " | " | " | " |
| IIb | " | " | " | " | " |
| IIa | $CO_2H\text{-}CH(NHCOC_6H_5)\text{-}(CH_2)_3\text{-}CO$ | " | " | " | " |
| IIb | " | " | " | " | " |

The following examples illustrate the invention:

EXAMPLE 1

7-(Thienyl-2-acetamido)-3-[2-(4-N,N-dimethylamino-phenylazo)-pyridinium-methyl]-3-cephem-4-carboxylic acid (PADAC)

A solution of 2.26 g (10 mmols) of trans-pyridine-2-azo-4'-dimethyl aniline (PADA) in 250 ml of acetone in a 1 liter, three-necked round flask provided with stirrer, thermometer and pH electrode is heated to 55° to 60° C. on a water bath. A solution of 4.0 g (10 mmols) of the sodium salt of cephalotin in 100 ml of water is added to the solution. After adjustment of a pH of 7.3 to 7.5 with saturated sodium bicarbonate solution, the reaction is followed by thin layer chromatogram (silica gel "Merck" F 254, system I: ethyl acetate, isopropanol/water 20:15:10). The desired product appears as violet band with $R_f$ 0.54.

When the reaction is terminated, the acetone is distilled off in vacuo and the aqueous residue is adjusted to pH 8. Undissolved substance (unreacted PADA) is separated and the aqueous phase is repeatedly extracted with ethyl acetate to remove residual PADA.

The aqueous phase is adjusted to pH 5.7 with dilute hydrochloric acid and repeatedly extracted with 1 volume each time of methylene chloride. The combined methylene chloride phases are concentrated in vacuo to 100 ml and the PADAC is precipitated by adding 300 ml of diethyl ether. The violet precipitate is filtered off on a frit, washed with a small amount of ether and dried. Yield 1.01 g of crude PADAC as a dark violet powder.

0.5 g of the crude PADAC are suspended in 20 ml of water and, while stirring and cooling, 0.1 N NaOH is added dropwise until a constant pH of 7 is reached. After lyophilization, 0.5 g of readily soluble sodium salt of PADAC is obtained.

EXAMPLE 2

7-(Thienyl-2-acetamido)-3-[2-(4-N,N-dimethylamino-phenylazo)-pyridinium-methyl]-3-cephem-4-carboxylic acid (PADAC)

In a 3 liter, four-necked flask provided with stirrer, thermometer and pH electrode, 40 g of sodium salt of cephalotin and 240 g of potassium iodide are dissolved in 1 liter of water. Separately, 22.6 g of PADA are dissolved in 500 ml of acetone and the solution is introduced into the flask. The pH of the mixture is adjusted to 6.5 and the flask is heated to 60° C. on a water bath (thermostat). During the reaction the pH is maintained at 6.5 by adding saturated sodium bicarbonate solution. After 5 hours the acetone is removed and unreacted PADA precipitated in the aqueous phase is separated by filtration. The aqueous phase is adjusted to pH 8 with sodium hydroxide solution and extracted three times, each time with 800 ml of ethyl acetate. The aqueous residue is adjusted to pH 3 with 1 N sulfuric acid and the precipitated PADAC is filtered off, washed with a small amount of water and dried in a high vacuum 11.8 g of violet powder are obtained.

Less pure PADAC can be obtained from the mother liquor by extracting twice, each time with 1 liter of methylene chloride. After evaporation of the methylene chloride to a volume of 200 ml, the product is precipitated with 600 ml of diethyl ether, filtered off with suction, washed with ether and dried. 5.2 g of crude PADAC are obtained.

1 g of crude PADAC is dissolved in 20 ml of a mixture of ethyl acetate, isopropanol and water in a proportion of 4:3:2 and charged to a column of 100 g of silica gel "Merck" 60, particle diameter 0.063 to 0.2 mm, flushed in with the same solvent system. After development with the system and separation of yellow-red first runnings, a violet zone is eluted containing the PADAC. After concentration by evaporation of the active fraction, the aqueous phase is lyophilized. 300 mg of pure PADAC are obtained. $\lambda_{max}$ 566 nm (5% acetonitrile) ($\epsilon = 42,200$) disappearing after addition of $\beta$-lactamase. IR: 3400, 1768 ($\beta$-lactam), 1666, 1600, 1562, 1540, 1485, 1390, 1350, 1330, 1300, 1269, 1225, 1150, 1105, 932, 910, 837, 785, 700 cm$^1$ NMR, (CD$_3$)$_2$SO: 9.0 (d, 1H, 6.5–8.0 (m), 5.5 (m), 5.0 (s), 3.7 (s), 3.1 (s) ppm.

EXAMPLE 3

7-(Thienyl-2-acetamido)-3-[2-(4-N-methyl-N-cyanoethyl-amino-phenylazo)-pyridinium-methyl]-3-cephem-4-carboxylic acid A solution of 80 g of sodium salt of cephalotin in 2 ml of water is mixed with a solution of 45 mg of pyridine-2-azo-4'-N-methyl-4'-N-cyanoethyl aniline (VI) in 1 ml of acetone. The mixture is adjusted to pH 6.5 and heated to 60° C. in a water bath. The course of the reaction is monitored by thin layer chromatography using system I according to Example 1. The reaction is terminated after 5 hours. The reaction mixture is extracted with ethyl acetate, the aqueous phase is adjusted to pH 3 with 1 N sulfuric acid and extracted with methylene chloride. The product is precipitated in the concentrated extract as a violet powder by addition of diethyl ether and dried.

Thin layer chromatography using system I: R$_f$ 0.54
$\lambda_{max}$ 543 nm (5% acetonitrile).

EXAMPLE 4

7-(Thienyl-2-acetamido)-3-[2-(4-N-acetoxyethyl-4-N-cyanoethyl-amino-phenylazo)-pyridinium-methyl]-3-cephem-4-carboxylic acid A solution of 80 mg of the sodium salt of cephalotin in 2 ml of water is reacted as described in Example 3 with a solution of 45 mg of pyridine-2-azo-4'-N-acetoxyethyl-N-cyanoethyl aniline and the reaction product is isolated. Violet powder.

Thin layer chromatography, system I: R$_f$ 0.54
$\lambda_{max}$ 520 nm (5% acrylonitrile).

EXAMPLE 5

7-(Thienyl-2-acetamido)-3-[2-(4-N,N-diacetoxyethyl-amino-phenylazo)-pyridinium-methyl]-3-cephem-4-carboxylic acid A solution of 160 g of the sodium salt of cephalotin in 4 ml of water is reacted as described in Example 3 with a solution of 90 mg of pyridine-2-azo-4'-N,N-diacetoxyethyl aniline and the reaction product is isolated. Violet powder.

Thin layer chromatography, system I: R$_f$ 0.64.
$\lambda_{max}$ 544 nm (5% acetonitrile).

EXAMPLE 6

7-(Thienyl-2-acetamido)-3-[3-(4-N,N-dimethylamino-phenylazo)-pyridinium-methyl]-3-cephem-4-carboxylic acid 80 mg of the sodium salt of cephalotin in 2 ml of water are reacted as described in Example 3 with 45 mg of pyridine-3-azo-4'-N,N-diethyl aniline and the reaction product is isolated. Red powder.

Thin layer chromatography, system I: R$_f$ 0.76
$\lambda_{max}$ 506 nm (5% acetonitrile).

EXAMPLE 7

7-(N-Benzoyl-5-amino-5-carboxy-valeroylamido)-3-[2-(4-N,N-dimethylamino-phenylazo)-pyridinium-methyl]-3-cephem-4-carboxylic acid 13.6 of the hexamethylene diamine salt of N-benzoyl-cephalosporin C are dissolved in 500 ml of water and mixed with a solution of 11.3 g of PADA in 250 ml of acetone. The mixture is adjusted to pH 6.5 and is heated for 5 hours to 60° C. on a water bath while stirring and maintaining the pH at 6.5 by adding saturated sodium carbonate solution. The reaction is monitored by thin layer chromatography (system I). When the reaction is terminated, the solution is cooled to 4° C. whereupon the unreacted PADA precipitates almost completely. After separation it can be used for further reactions. The solution is concentrated and the aqueous phase (300 ml) is extracted once with 1 volume of ethyl acetate. Next, a pH of 3 is adjusted with 1 N sulfuric acid, the aqueous phase is extracted three times, each time with 1 volume of butanol. The butanol is concentrated to about 60 ml under reduced pressure and the reaction product is precipitated by adding 2 to 3 volumes of diethyl ether. 13 g of crude title compound are obtained as a light violet powder which still contains considerable amounts of N-benzoyl-cephalosporin C.

1.2 g of the crude product are dissolved in 20 ml of a mixture of ethyl acetate, isopropanol and water in a proportion of 4:3:2 and charged to a column of 100 g of silica gel "Merck" 60, particle size 0.063–0.2 mm, flushed in with the same system, and developed with the system. The violet zone containing the desired product is collected separately, concentrated by evaporation and the aqueous phase is lyophilized. 68 mg of highly purified title compound are obtained in the form of a violet powder.

Thin layer chromatogram, system I: R$_f$ 0.33
$\lambda_{max}$ 566 (5% acetonitrile)

EXAMPLE 8

7-Amino-3-[2-(4-N,N-dimethylamino-phenylazo)-pyridinium-methyl]-3-cephem-4-carboxylic acid A solution of 1.36 g of 7-aminocephalosporanic acid in 50 ml of water is combined with a solution of 1.13 g of PADA in 25 ml of acetone and the mixture is adjusted to pH 6.5. The reaction on a water bath at 60° C. is terminated after 3 hours. After distillation of the acetone, the aqueous phase is extracted twice, each time with 1 volume of ethyl acetate, concentrated by evaporation to 15 ml and 110 ml of acetone are added. The precipitated product is centrifuged, washed with acetone and dried. Yield: 1.2 g of crude title compound as violet powder.

200 ml of the crude product obtained are dissolved in 5 ml of water and the solution is charged to a column of 10 ml of adsorption resin Diaion HP-20, flushed in with water, and developed with 50 ml each of the following eluents: water, 10% acetonitrile, 20% acetonitrile. The desired product is eluted with 10% and 20% acetonitrile, the active fractions are concentrated by evaporation in vacuo. 51 mg of highly purified title compound are obtained as violet powder.

Thin layer chromatography, system I: $R_f$ 0.15
$\lambda_{max}$ 566 nm (5% acetonitrile)

EXAMPLE 9

7-Phenylacetamido-3-[2-(4-N,N-dimethylamino-phenylazo)-pyridinium-methyl]-3-cephem-4-carboxylic acid 159 mg (0.5 millimol) of 7-amino-3-[2-(4-N,N-dimethylamino-phenylazo)-pyridinium-methyl]-3-cephem-4-carboxylic acid obtained as described in Example 8 and 120 mg of sodium carbonate are dissolved in 8 ml of water and 10 ml of acetone. The solution is cooled in iced water and a solution of 80 mg of phenacetyl chloride in 1 ml of acetone is added. After stirring for 1 hour at 0° C., another 16 mg of phenacetyl chloride in 0.2 ml of acetone are added. After a further hour at 0° C., the mixture is diluted with 20 ml of water, the acetone is removed in vacuo and a pH of 8 is adjusted. After twofold extraction with ethyl acetate, the aqueous phase is adjusted to pH 1.0 and extracted with n-butanol until the aqueous solution has become colorless. The combined butanol extracts are combined with double the amount of chloroform and evaporated to dryness. The residue is extracted twice with ethanol. After evaporation of the ethanol, 110 mg of the title compound are obtained as violet powder containing phenylacetic acid is impurity.

Thin layer chromatography, system I: $R_f$ 0.53
$\lambda_{max}$ 566 nm (5% acetonitrile).

EXAMPLE 10

7-(Thienyl-2-acetamido)-3-[2-(4-N,N-dimethylamino-phenylazo)-pyridinium-methyl]-3-cephem-4-carboxylic acid 159 mg of 7-amino-3-[2-(4-N,N-dimethylamino-phenylazo)-pyridinium-methyl]-3-cephem-4-carboxylic acid obtained as described in Example 8 are reacted with 80 mg of thienyl-2-acetyl chloride in the manner described in Example 9. 90 mg of PADAC are obtained, contaminated with thienyl-acetic acid.

Thin layer chromatography and $\lambda_{max}$ as defined in Example 2.

EXAMPLE 11

7-Phenoxyacetamido-3-[2-(4-N,N-dimethylamino-phenylazo)-pyridinium-methyl]-3-cephem-4-carboxylic acid 159 mg of 7-amino-3-[2-(4-N,N-dimethylamino-phenylazo)-pyridinium-methyl]-3-cephem-4-carboxylic acid obtained as described in Example 8 and 85 mg of phenoxyacetyl chloride are reacted in the manner described in Example 9 and yield 150 mg of violet title compound, contaminated with phenoxyacetic acid.

Thin layer chromatography, system I: $R_f$ 0.51
$\lambda_{max}$ 566 nm (5% acetonitrile).

EXAMPLE 12

7-(Thienyl-2-acetamido)-3-[2-(4-N-ethyl-4-N-carboxyethylamino-phenylazo)-pyridinium-methyl]-3-cephem-4-carboxylic acid.

400 mg of the sodium salt of cephalotin are reacted as described in Example 3 with 255 mg of pyridine-2-azo-4'-N-ethyl-4'-N carboxyethyl aniline and the reaction product is isolated. Violet powder.

Thin layer chromatography, system I: $R_f$ 0.48
$\lambda_{max}$ 566 nm (5% acetonitrile).

For conversion into the readily water-soluble sodium salt, the product is suspended in water, the pH of the suspension is adjusted to 7 by cautiously adding dilute NaOH and stirring and the solution is lyophilized.

EXAMPLE 13

7-(Thienyl-2-acetamido)-3-[2-(4-N-ethyl-4-N-carboxyethylamino-phenylazo)-pyridinium-methyl]-3-cephem-4-carboxylic acid 200 mg of the sodium salt of cephalotin are reacted with 112 mg of pyridine-3-azo-4'-N-ethyl-4'-N-carboxyethyl aniline in the manner described in Example 3 and the reaction product is isolated. Red Powder.

Thin layer chromatography, system I: $R_f$ 0.53.
$\lambda_{max}$ 499 nm (5% acetonitrile).

The product is converted into the sodium salt in the manner described in Example 12.

EXAMPLE 14

7-(Thienyl-2-acetamido)-3-[3-(8-N-carboxyethylamino-quinolin-5-azo)-pyridinium-methyl]-3-cephem-4-carboxylic acid 240 mg of the sodium salt of cephalotin are reacted with 180 mg of pyridine 3-azo-5'-(8'-carboxyethylamino)-quinoline in the manner described in Example 3 and the reaction product is isolated. Red-violet powder.

Thin layer chromatography, system I: $R_f$ 0.40.
$\lambda_{max}$ 516 nm (5% acetonitrile)

The product is converted into the water-soluble sodium salt in the manner described in Example 12.

What is claimed is:
1. A cephalosporin of the formula wherein
$R^1$ is hydrogen, formyl, or $$R''-\underset{\underset{R'''}{|}}{\overset{\overset{R'}{|}}{C}}-CO-,$$

wherein in turn
$R'$ is hydrogen; alkyl having 1 to 4 carbon atoms; such alkyl substituted by chlorine, by bromine, by cyano, by hydroxy, or by alkoxy having 1 to 4 carbon atoms; or is ω-carboxyalkyl; ω-carboxy-ω-aminoalkyl; ω-carboxy-ω-benzoylaminoalkyl; cycloalkyl or cyclalkenyl having 5 to 7 carbon atoms; phenyl; phenyloxy; or phenyl or phenyloxy mono- or di-substituted by alkyl having 1 to 4 carbon atoms, by hydroxy, by alkoxy having 1 to 4 carbon atoms, by alkanoyloxy having 1 to 4 carbon atoms, by fluorine, by chlorine, by carboxy, by sulfoxy, by amino, or by alkanoylamino having 1 to 4 carbon atoms; or R' is 2-pyridon-1-yl; 4-pyridon-1-yl; 3,5-dichloro-pyridon-1-yl; 2-thienyl; 3-thienyl; 2-furyl; 3-furyl; tetrazolyl; or is thiazolyl of the formula

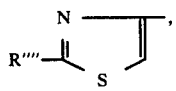

wherein R'''' is alkyl having 1 to 4 carbon atoms, formamido, acetamido, chloroacetamido, bromoacetamido, or trifluoroacetamido; or R' is 2-methyl-1,3,4-thiadiazol-5-yl-thio; or is 2-amino-1,3,4-thiadiazol-5-yl-thio;

R'' and R''', taken together, are oxygen, or, taken alone, are the same or different and are hydrogen; alkyl having 1 to 4 carbon atoms; hydroxy; alkanoyloxy having 1 to 4 carbon atoms; alkoxy having 1 to 4 carbon atoms; amino; alkylamino; alkylamino mono- or di-substituted by p-methoxyphenyl or mono-, di-, or tri-substituted by phenyl; alkoxycarbonyl having 1 to 4 carbon atoms in the alkyl group; chlorine; bromine; cyano; sulfoxy; aminosulfonyl; or are acylamino selected from the group consisting of formylamino, acetylamino, chloroacetylamino, bromoacetylamino, benzoylamino, tert.butoxycarbonylamino, 2,2,2-trichloroethoxy-carbonylamino, 4-hydroxy-1,5-naphthyridin-2-carbonylamino, 3-hydroxy-pyridazin-4-carbonylamino, imidazolidin-2-on-1-yl-carbonylamino, (3-methyl-sulfonyl-imidazolidin-2-on-1-yl) carbonylamino, and (4-ethyl-piperazin-2,3-dion-1-yl) carbonylamino;

$R^4$ and $R^5$ are the same or different and are hydrogen; alkyl having 1 to 4 carbon atoms; or alkyl having 1 to 4 carbon atoms substituted by cyano, by carboxy, by alkoxy having 1 to 4 carbon atoms, by hydroxy, by alkanoyloxy having 1 to 4 carbon atoms, by aminocarbonyl, by sulfoxy, or by chloro; and $R^{3'}$ is two hydrogen atoms or is benzo, pyrido, thieno, pyrimidino, or thiazolo.

2. A cephalosporin as in claim 1 wherein $R^1$ is thienylacetyl.

3. 7-(thienyl-2-acetamido)-3-[2-(4-N,N-dimethylaminophenylazo)-pyridinium-methyl]-3-cephem-4carboxylic acid.

* * * * *